United States Patent [19]
Moore, Jr.

[11] Patent Number: 5,914,104
[45] Date of Patent: *Jun. 22, 1999

[54] USE OF ALUM TO INHIBIT AMMONIA VOLATILIZATION AND TO DECREASE PHOSPHORUS SOLUBILITY IN POULTRY LITTER

[75] Inventor: Philip A. Moore, Jr., Fayetteville, Ark.

[73] Assignee: Trustees of the University of Arkansas, Little Rock, Ark.

[ * ] Notice: This patent is subject to a terminal disclaimer.

[21] Appl. No.: 08/852,273

[22] Filed: May 7, 1997

Related U.S. Application Data

[63] Continuation-in-part of application No. 08/735,103, Oct. 22, 1996, which is a continuation-in-part of application No. 08/437,991, May 10, 1995, Pat. No. 5,622,697, which is a continuation of application No. 08/129,742, Sep. 30, 1993, abandoned.

[51] Int. Cl.⁶ .................................................... A61L 9/00
[52] U.S. Cl. ...................... 424/76.6; 119/171; 210/906; 424/646; 424/647; 424/648; 424/663; 424/682; 424/687; 424/693; 424/698; 424/709
[58] Field of Search ................... 424/76.6, 682, 424/687, 693, 698, 646, 647, 648, 709, 663; 119/171; 210/906

[56] References Cited

U.S. PATENT DOCUMENTS

| | | |
|---|---|---|
| 3,029,783 | 4/1962 | Sawyer et al. ............... 119/1 |
| 4,028,238 | 6/1977 | Allan .......................... 210/53 |
| 4,209,335 | 6/1980 | Katayama et al. ........... 106/89 |
| 5,039,481 | 8/1991 | Pacifici et al. ............... 422/4 |

FOREIGN PATENT DOCUMENTS

| | | |
|---|---|---|
| 0 156 924 B1 | 10/1985 | European Pat. Off. . |
| 0 557 078 A1 | 8/1993 | European Pat. Off. . |
| 84/02334 | 6/1984 | WIPO . |

OTHER PUBLICATIONS

Chemical Abstracts 112:204041, "Deodorant Composition for Air", Jun. 1989.

Chemical Abstracts 104:173975, "Manure Deodorizing Agent", Dec. 1985.

*Primary Examiner*—Frederick Krass
*Attorney, Agent, or Firm*—Arthur J. Plantamura; Needle & Rosenberg, PC

[57] ABSTRACT

Short term control of ammonia volatilization from animal manures is provided by surface treatment with aluminum sulfate. The aluminum sulfate may be applied to manure or manure receiving surfaces in an animal rearing facility in solid or liquid form. The control of atmospheric ammonia levels in animal rearing facilities to preferably less than about 25 ppm ammonia can be achieved by surface treatment employing amounts of alum as low as 0.5% by weight alum based on manure present.

13 Claims, 1 Drawing Sheet

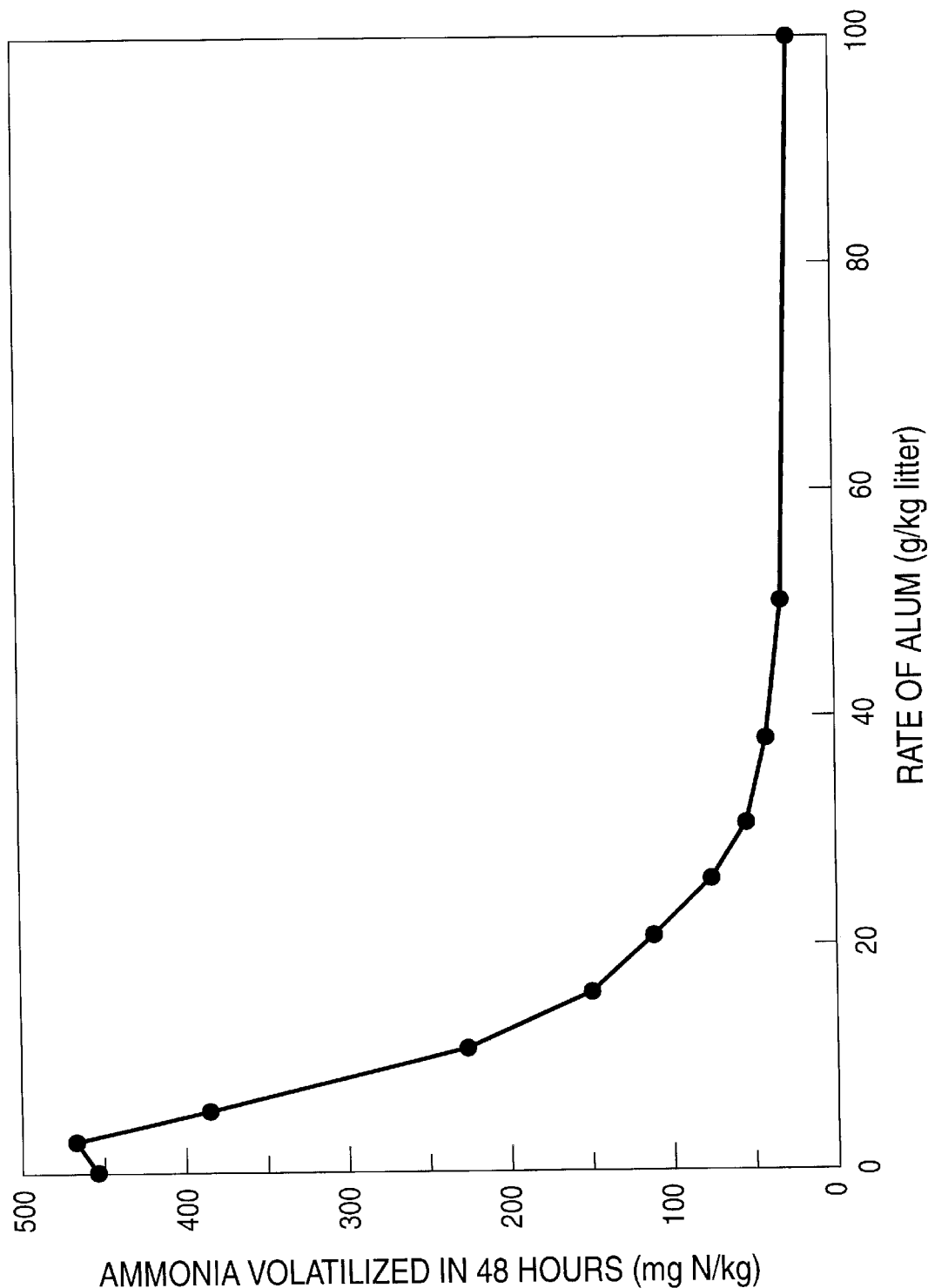

USE OF ALUM TO INHIBIT AMMONIA VOLATILIZATION AND TO DECREASE PHOSPHORUS SOLUBILITY IN POULTRY LITTER

CROSS REFERENCE TO RELATED APPLICATIONS

This application is a continuation-in-part of prior application Ser. No. 08/735,103, filed Oct. 22, 1996, which is a continuation-in-part of prior application Ser. No. 08/437, 991, filed May 10, 1995 now U.S. Pat. No. 5,622,697), which is a continuation of prior application Ser. No. 08/129, 742, filed Sep. 30, 1993 abandoned), the disclosures of which are hereby incorporated by reference.

BACKGROUND OF THE INVENTION

In my prior application, Ser. No. 08/437,991, filed May 10, 1995, now U.S. Pat. No. 5,622,697, a method for inhibiting ammonia volatilization in animal manure, particularly poultry litter for long time periods (3–6 weeks) is disclosed. The method comprises the steps of adding alum (aluminum sulfate) to poultry litter (comprising poultry manure, bedding material, spilled food and feathers) and mixing. In accordance with this application, alum is added in sufficient quantities to reduce the pH of alum/poultry litter base composition to less than 7.0, and preferably, alum may be added a rate of 5% to about 25% by weight based on manure.

In my second above-mentioned patent application, Ser. No. 08/735,103, filed Oct. 22, 1996, a method for rearing animals, including, for example, laying hens, is described wherein animals are raised in a so-called high-rise facility including a raised perforated animal rearing platform and a lower manure collection area. In accordance with the method described in this application, a liquid alum solution is delivered to the manure collection area and sprayed onto a surface of the collected manure to improve, inter alia, the atmospheric conditions of the animal rearing area. In an embodiment of the method described in this latter application, the alum solution, containing from about 1 to about 50% by weight alum, is applied at a rate of about 50 to about 250 g of $Al_2(SO_4)_3$ $H_2O$ per kg of manure as it accumulates.

In the present application, a new and improved method is provided including the step of adding alum to poultry litter or manure, wherein the alum is mixed with the surface portion or layer of the poultry litter or manure, for example to a surface depth of from about 0 to about 10 cm. Using this procedure, the amount of alum needed to reduce ammonia volatilization can be dramatically reduced, particularly if the user is only interested in controlling ammonia volatilization for short time periods (days to weeks). The lowest rate of alum addition needed to reduce ammonia volatilization using this technique is about 0.5%, rather than 5%.

SUMMARY OF THE INVENTION

The present invention relates to a method for reducing ammonia levels in animal rearing facilities, particularly poultry houses, by adding alum to a surface layer of manure or poultry litter composition already present in the house.

It will be understood that the following theoretical discussion should not be interpreted as limiting the present invention to a particular theory or explanation.

Solid or liquid alum will lower the pH of the manure, converting ammonia ($NH_3$) to ammonium ($NH_4^+$), which will combine with sulfate ($SO_4^{2-}$) to form ammonium sulfate [$(NH_4)_2SO_4$], which is a water soluble nitrogen fertilizer. Thus, this process increases the fertilizer value of the manure, while improving the atmosphere inside the animal rearing facility for both animals and humans alike.

Dry alum may be broadcast applied onto animal manures, such as poultry manure or litter composition present in a growing facility, by several different methods, including, but not limited to the following; (1) by hand, (2) using a fertilizer spreader, (3) using a manure spreader, and/or (4) using a litter truck. Liquid alum may be applied using the following methods; (1) backpack sprayer, (2) boom sprayer pulled behind a truck or tractor, and/or (3) a system of stationary or moving spraying devices permanently attached to the house.

Dry or liquid alum may be applied periodically as needed to lower atmospheric ammonia levels suitable for maximizing animal husbandry. For most animals, this level is approximately 25 ppm $NH_3$.

The amount of alum added to a surface portion of the manure will depend on the number of animals in the house and the subsequent amount of manure generated, which will control the amount of ammonia volatilization. Alum will be added at a rate of 0.5 to 250 g $Al_2(SO_4)_3$ .$14H_2O$ per kg of manure (on a dry weight basis). Although the preferred application rate to control ammonia for long time periods is approximately 100 grams $Al_2(SO_4)_3.14H_2O$ per kg of manure (equivalent to approximately 10% alum by weight), much lower rates of from about 0.5 to about 50 grams of alum per kg litter or manure will reduce ammonia losses, at least for a short time period.

One example of this new method would be a broiler house in which 20,000 broilers are grown. In this scenario, about 20 tons of broiler litter, i.e., a mixture of manure, bedding material, spilled feed and feathers, is generated by each and every flock, sometimes referred to as a growout. After each flock of chickens is harvested, most poultry producers either "de-cake" or roto-till the litter. De-caking is a process whereby the wet hardened manure on the surface (referred to as cake by growers) is removed mechanically by a machine that picks up the litter, sifts it, and removes large particles (usually greater than 1 inch in diameter). After de-caking or tilling, in accordance with an embodiment of this invention, dry or liquid alum is applied to the litter. If dry alum is applied, rates as low as 5 g/kg litter can be used, if the producer only mixes the alum in the surface of the litter (0–10 cm), with the preferred depth of mixing the top 0–2 cm. Although 5 g alum/kg would lower ammonia losses, higher rates would work even better. If liquid alum is being used, incorporation by tilling is not necessary.

Poultry producers usually only add fresh bedding material after a "total cleanout" (i.e.—after all the litter has been removed from the house). Some producers may add new bedding material between growouts. Bedding materials vary with the region, but are usually wood shavings, sawdust, rice hulls, peanut hulls, straw, recycled paper, or a similar substance. If new bedding is going to be applied, then alum can be applied to the litter after de-caking without incorporation into the litter. It is important that the alum be totally covered up with bedding material if surface application without incorporation is utilized.

In accordance with the new and improved method of the present invention, ammonia volatilization from manure may be inhibited by applying as little as 200 pounds of alum to a commercial broiler house containing 20,000 birds. However, higher doses (400 to 4,000 pounds) will result in ammonia control for much longer time periods and result in much lower atmospheric ammonia concentrations with less ventilation.

Many poultry producers only use one-third or one-half of the house to rear animals when they are young. This is usually referred to as the "brooding chamber" or "brood end of the house". When this management practice is being employed, the producer only heats and/or cools that portion of the rearing facility where the animals are. In this scenario, it may be more cost effective for the producer to apply alum only to the brood portion of the house, since the atmosphere from the other side of the house is not being mixed with this atmosphere. This can effectively reduce the amount of alum by 50 to 66% (if only one-half to one-third of the house is being used).

BRIEF DESCRIPTION OF THE DRAWING

FIG. 1 is a graph of the results obtained in Example 1, with ammonia volatilized in 48 hours plotted against rate of alum addition.

Another source of ammonia in animal rearing facilities is the dirt floor underneath the litter. Urine and/or spilled water can transport nitrogen containing compounds, such as urea or uric acid, downward into the soil under the litter. To further reduce ammonia levels in animal rearing facilities, producers can apply dry or liquid alum to this floor after the litter has been removed during a total cleanout.

In accordance with an embodiment, other acids may be combined with or separately applied together with the alum to improve its' effectiveness or lower the cost. Inorganic or organic acids may be added to dry or liquid alum for this purpose.

Although the described embodiments of the present invention have focused on treating poultry manure or litter, it is contemplated that the addition of alum as described herein would be applicable to other types of animal manures.

DETAILED DESCRIPTION OF THE PREFERRED EMBODIMENTS

By way of example, and not limitation, the following example serves to further illustrate the present invention to those skilled in this art.

EXAMPLE 1

Methods and Materials

Fresh poultry litter was collected from a commercial poultry house in Northwest Arkansas. The litter was passed through a 0.5 cm mesh and mixed. One hundred grams of poultry litter (moist weight) was weighed out into 44 containers with air-tight lids. Eleven alum treatments were utilized in this study. The treatments were as follows:

| | g alum/100 g | lbs alum/house | g alum/kg | % alum by weight |
|---|---|---|---|---|
| 1. | 0 | 0 | 0 | 0 |
| 2. | 0.25 | 100 | 2.5 | 0.25 |
| 3. | 0.50 | 200 | 5.0 | 0.50 |
| 4. | 1.00 | 400 | 10.0 | 1.00 |
| 5. | 1.50 | 600 | 15.0 | 1.50 |
| 6. | 2.00 | 800 | 20.0 | 2.00 |
| 7. | 2.50 | 1,000 | 25.0 | 2.50 |
| 8. | 3.00 | 1,200 | 30.0 | 3.00 |
| 9. | 3.75 | 1,500 | 37.5 | 3.75 |
| 10. | 5.00 | 2,000 | 50.0 | 5.00 |
| 11. | 10.0 | 4,000 | 100.0 | 10.0 |

There were four replications per treatment. The treatments were mixed into the top 1 cm of poultry litter only.

The containers were equipped with air inflows and outflows. Ammonia-free air was passed through each chamber and any ammonia volatilized from the litter was trapped in two consecutive traps containing 30 ml of boric acid solution. At each sampling period, the boric acid was removed and titrated with 0.10 N HCl to determine the ammonia content. After the titration, the flasks were replaced with new boric acid solutions. Sampling times were at 4, 20 and 48 hours.

Results

The results of this experiment are shown in FIG. 1. These data clearly indicate that very low rates of alum can inhibit ammonia volatilization from poultry litter when mixed into the top layer of the litter. Rates as low as 5 grams alum/kg litter reduced ammonia volatilization, compared to the control. This would be equivalent to adding 200 pounds of $Al_2(SO_4)_3 \cdot 14H_2O$ to a 16,000 ft.$^2$ poultry house in which 20,000 birds were produced each flock. Higher rates of alum, such as the 50 and 100 g/kg rate were obviously the most effective. However, rates as low as 20–25 g alum/kg litter, which would be equivalent to about 800 to 1,000 lbs alum applied to a house with 20,000 birds, were almost as effective as the highest rates.

Several factors may cause the lower rates of alum to be more cost-effective than the higher rates. Poultry are much more susceptible to high levels of ammonia when they are young (1 to 28 days) than when they are older. Therefore, reducing ammonia levels early on has more impact on the birds health than later. Since the higher rates would only be protecting older birds, they may be less cost-effective.

Another parameter effected by alum is the amount of ventilation needed in an animal rearing facility. When poultry are young, the temperature inside the house must be very warm (>87° F.). These high temperatures result in larger quantities of ammonia being volatilized and, hence, higher levels of ammonia in the house. Therefore, more ventilation is required to remove ammonia. Unfortunately, producers usually ventilate less early on because they are trying to keep the birds warm and when they increase ventilation, they increase the amount of cold air that has to be heated, which increases energy usage. As birds age, they develop more feathers, which insulates their body, retaining body heat better. As a result, the inside temperature of the houses can be lowered dramatically (to below 70° F.) after a few weeks. It is easier to control ammonia at this time, since the ventilation can be increased without having to heat as much as would be required to maintain a high temperature. This may be another reason it is more cost-effective to only control ammonia early in the life cycle, which would allow lower rates of alum to be used.

What is claimed is:

1. A method for inhibiting ammonia volatilization from animal manure comprising the steps of:

applying aluminum sulfate to a surface portion of a sample of animal manure in an amount sufficient to reduce the pH of the sample and thereby inhibit ammonia volatilization from said sample for at least forty eight hours, as compared to a corresponding sample of untreated animal manure.

2. A method as defined in claim 1, wherein aluminum sulfate is applied as a liquid or a solid.

3. A method as defined in claim 1, wherein the amount of aluminum sulfate applied is sufficient to change a pH of the surface portion to a pH of less than or equal to 7.5.

4. A method as defined in claim 1, wherein the amount of aluminum sulfate applied is from about 0.5% to about 25% by weight of said sample.

5. A method as defined in claim 1, wherein said sample is obtained from broilers, breeders, laying hens, turkeys, ducks, swine, sheep, cattle, dairy cows, horses or rabbits.

6. A method for controlling atmospheric ammonia levels in an animal rearing facility comprising the steps of:

applying aluminum sulfate to a surface portion of a manure receiving surface in an animal rearing facility in an amount sufficient to reduce the pH of the sample and thereby inhibit ammonia volatilization from the manure receiving surface for at least forty eight hours to control atmospheric ammonia levels in said animal rearing facility at or below a selected level, said manure receiving surface comprising previously deposited manure.

7. A method as defined in claim 6, wherein aluminum sulfate is applied as a liquid or a solid.

8. A method as defined in claim 6, wherein the selected level is about 25 ppm or less of ammonia.

9. A method as defined in claim 6, wherein said manure receiving surface comprises a dirt floor.

10. A method as defined in claim 6, wherein said manure receiving surface comprises a mixture of previously deposited manure and bedding material.

11. A method as defined in claim 6, further comprising admixing the applied aluminum sulfate into the surface portion to a depth of about 10 cm or less.

12. A method as defined in claim 6, wherein said animal rearing facility is a facility for raising chickens, turkeys, ducks, swine, sheep, cattle, dairy cows, horses or rabbits.

13. A method as defined in claim 6, wherein said animal rearing facility comprises a roof over an enclosure.

* * * * *

UNITED STATES PATENT AND TRADEMARK OFFICE
CERTIFICATE OF CORRECTION

PATENT NO. : 5,914,104
DATED : June 22, 1999
INVENTOR(S) : Philip A. Moore, Jr.

It is certified that error appears in the above-identified patent and that said Letters Patent is hereby corrected as shown below:

Title page, item [73]; should read "Trustees of The University of Arkansas and The United States of America".

Signed and Sealed this

Fourteenth Day of December, 1999

Attest:

Attesting Officer

Q. TODD DICKINSON

Acting Commissioner of Patents and Trademarks